(12) United States Patent
Baugh et al.

(10) Patent No.: US 6,541,262 B1
(45) Date of Patent: Apr. 1, 2003

(54) METHOD AND DEVICE FOR TESTING A SAMPLE OF FRESH WHOLE BLOOD

(75) Inventors: Robert F. Baugh, Parker, CO (US); Julie S. Johnston-Eaton, Conifer, CO (US); Colleen Lutz, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/560,470

(22) Filed: Apr. 28, 2000

(51) Int. Cl.[7] .............................................. G01N 33/86
(52) U.S. Cl. ...................... 436/69; 422/73; 600/369; 73/64.41
(58) Field of Search ........................... 436/63, 69, 164, 436/165; 422/73; 600/368, 369; 73/64.41

(56) References Cited

U.S. PATENT DOCUMENTS

| | | | |
|---|---|---|---|
| 4,067,777 A | 1/1978 | Innerfield | 195/103 |
| 4,533,519 A | 8/1985 | Baugh et al. | 422/73 |
| 4,599,219 A | 7/1986 | Cooper et al. | 422/61 |
| 4,871,677 A | 10/1989 | Baugh et al. | 436/69 |
| 5,302,348 A | 4/1994 | Cusack et al. | 422/73 |
| 5,314,826 A | 5/1994 | Baugh | 436/69 |
| 5,366,869 A | 11/1994 | Goldstein | 435/13 |
| 5,441,892 A | 8/1995 | Baugh | 436/69 |
| 5,534,226 A | 7/1996 | Gavin et al. | 422/73 |
| 5,591,403 A | 1/1997 | Gavin et al. | 422/73 |
| 5,686,659 A | 11/1997 | Neel et al. | 73/53.01 |
| 5,789,664 A | 8/1998 | Neel et al. | 73/53.01 |
| 5,800,781 A | 9/1998 | Gavin et al. | 422/73 |
| 5,925,319 A | 7/1999 | Baugh et al. | 422/73 |
| 5,951,951 A | 9/1999 | Lane et al. | 422/73 |
| 5,972,712 A | * 10/1999 | Baugh et al. | 436/69 |
| 6,221,672 B1 | * 4/2001 | Baugh et al. | 436/69 |

FOREIGN PATENT DOCUMENTS

| | | | |
|---|---|---|---|
| WO | 97/41432 | * 11/1997 | |
| WO | WO 00/02054 | 1/2000 | |

OTHER PUBLICATIONS

Medtronic Science & Technology Journal, Oct. 1996, Adrian Wilson, Ph.D., et al.—HemoStatus—A New Diagnostic Test For Platelet Function.

Medtronic Trade Literature, 1996, UC9503190EE, Autologous Blood Component Systems—Sequstra 1000.

* cited by examiner

Primary Examiner—Maureen M. Wallenhorst
(74) Attorney, Agent, or Firm—Thomas G. Berry; Daniel W. Latham

(57) ABSTRACT

A method and device for testing a sample of fresh whole blood. In particular the present invention provides a method and device for testing a sample of fresh whole blood to determine whether a patient would benefit from the administration of a blood factor (such as AT III.)

15 Claims, 4 Drawing Sheets

METHOD AND DEVICE FOR TESTING A SAMPLE OF FRESH WHOLE BLOOD

FIELD OF THE INVENTION

The management of hemostasis (also known as blood clotting) is an important requirement for a successful surgery. The exposure of blood to foreign surfaces, which often occurs during surgery, as well as the surgery itself can induce the activation of the clotting mechanism.

The clotting mechanism can be mediated in a variety of ways. One of the more common methods of mediating coagulation is to administer heparin.

The administration of heparin, however, must be done carefully. Care is required because the response of any one patient to a particular dose of heparin is highly variable, depending upon the particular physiology of each patient. Thus, it is often quite necessary for physicians or other care givers to understand the exact blood physiology of a patient such that a proper heparin dosage may be administered.

The Medtronic HMS Plus™ hemostasis management system may be used to measure many blood parameters, including activated clotting time (ACT). The Medtronic HMS Plus™ system uses an ACT to measure a heparin dose response methodology. The heparin dose response curve may be seen in FIG. 1.

The heparin dose response requires a small sample of whole blood from a patient. The whole blood is introduced into particular assay channels or vials, at least one (and preferably two) of the assay vials having no heparin reagent, at least one (and preferably two) more assay vials having a heparin reagent concentration of A and at least one (and preferably two) more assay vials having a heparin reagent concentration of B, where the concentration denoted as A is different from the concentration denoted as B.

The test begins by introducing the same volume of blood into each of the channels or vials. Thereafter the blood is mixed (preferably using a plunger.) The blood clots in each of the channels or vials at differing times. The clot is measured by timing the descent rate of the plunger. Ultimately, the clotting of each of the vials or channels may graphed as shown in FIG. 1, where line 1 may be draw through the three data points created by the formation of a blood clot in each channel or vial. That is, blood without any reagents (depicted here as data point $DP_O$), blood with heparin reagent concentration A (depicted here as data point $DP_A$) and blood with heparin reagent concentration B (depicted here as data point $DP_B$). As seen, the heparin dose response is a linear function when the ACT is used to initiate coagulation.

The heparin dose response line varies from patient to patient. That is, the linear heparin dose response seen in FIG. 1 has differing slopes for differing patients. Patients may have a heparin dose response line having slopes such as those seen as line 1' (very low slope) or line 1" (very high slope.) Generally speaking, the flatter or lower the slope of the line the more heparin resistant the patient is. Heparin resistant patients may have a variety of factors at work accounting for the heparin resistance. For example, these patients may have mechanisms which complex or bind the heparin, not allowing the heparin to inhibit blood coagulation. There may also be mechanisms present in the patient that rapidly eliminate the heparin. Finally, these patients may be heparin resistant due to their levels of the serine protease inhibitor antithrombin III (AT III). Heparin is a catalyst, that is, it helps prevent coagulation by accelerating the natural anticoagulant mechanisms present in the patient. The primary mechanism is the inhibition of thrombin, the primary protease of blood coagulation, by AT III. Without adequate amounts of AT III, heparin is ineffective in prevent blood coagulation.

AT III targets proteases of the coagulation cascade, and in particular thrombin. Heparin accelerates the rate with which AT III inhibits the proteases. Thus, without the presence of ACT III, the anticoagulant activity of heparin is severely diminished. The differences in which individuals respond to heparin may be affected by the differences in their AT III levels. Thus, a goal of the present system is to provide a method of assessing the heparin dose response while further accessing whether such heparin dose response is attributable to presence or absence of sufficient levels of AT III within the patient.

Thus there exists a need for a method and device which may reliably sense the heparin dose response of fresh whole blood as well as whether the fresh whole blood (and thus patient) has, or requires additional, AT III.

SUMMARY OF THE INVENTION

The present invention provides a method and device for testing a sample of fresh whole blood. In particular the present invention provides a method and device for testing a sample of fresh whole blood to determine whether a patient would benefit from the administration of a blood factor (such as AT III) Patients may benefit from such an administration both prior to surgery as well as for other reasons, such as if a patient suffers from acute myocardial ischemia. The blood factor may be a factor which is involved with the coagulation cascade. In the preferred embodiment the blood factor is the serine protease inhibitor Antithrombin III (AT III). The method of the present invention determines whether a patient would benefit from the administration of a blood factor prior to surgery through the testing of a whole blood sample within at least three testing channels, a first channel, a second channel and a third channel. Preferably the at least three channels are provided within an integral cartridge. The first channel is a control channel and contains a portion of a single whole blood sample without any additives. The second channel contains a portion of the single whole blood sample along with a thrombotic/hemorrhagic agent. The third channel contains a portion of a the single whole blood sample along with the thrombotic/hemorrhagic agent and a blood factor which is involved in controlling the coagulation cascade. In the preferred embodiment the thrombotic/hemorrhagic agent which may be selected from glycosaminoglycans which have the anticoagulant sequence which binds to the blood factor which is involved in controlling the coagulation cascade. In the preferred embodiment the thrombotic/hemorrhagic agent is heparin and the blood factor which is involved in controlling the coagulation cascade is AT III. Each channel is provided with a device for assessing when a clot is formed. The time for the formation of a clot in each channel may be used to determine whether the patient would benefit from the administration of a blood factor prior to surgery. In the preferred embodiment the method may be performed within the Medtronic Hepcon HMS Plus™ Hemostasis Management System. The device of the present invention may be practiced through a test cartridge used within the Medtronic Hepcon HMS Plus™ Hemostasis Management System but modified to contain the appropriate reagents, identified above, in the testing cartridges.

The present invention, furthermore, is advantageous, as it performs such tests on a sample of fresh whole blood, as opposed to citrated blood. The use of fresh whole blood as opposed to citrated blood is generally preferred, since the inclusion of citrate into blood affects blood characteristics, and thus the test. In particular, citrate causes platelets to activate. Over time, moreover, citrate itself affects clotting. Both of these affects may lead to misleading test results, possible affecting patient care. In view of these deficiencies with citrated blood, past efforts have been made to compensate or mediate the affects of citrate in blood. See, for example, Baugh et al. U.S. Pat. No. 4,871,677 "Method Of Collecting And Analyzing A Sample Of Blood When Monitoring Heparin Therapy." Such past efforts, while of some benefit, have not met with ideal results.

The FIGS are not necessarily to scale.

DETAILED DESCRIPTION OF THE FIGURES

Figure 1:
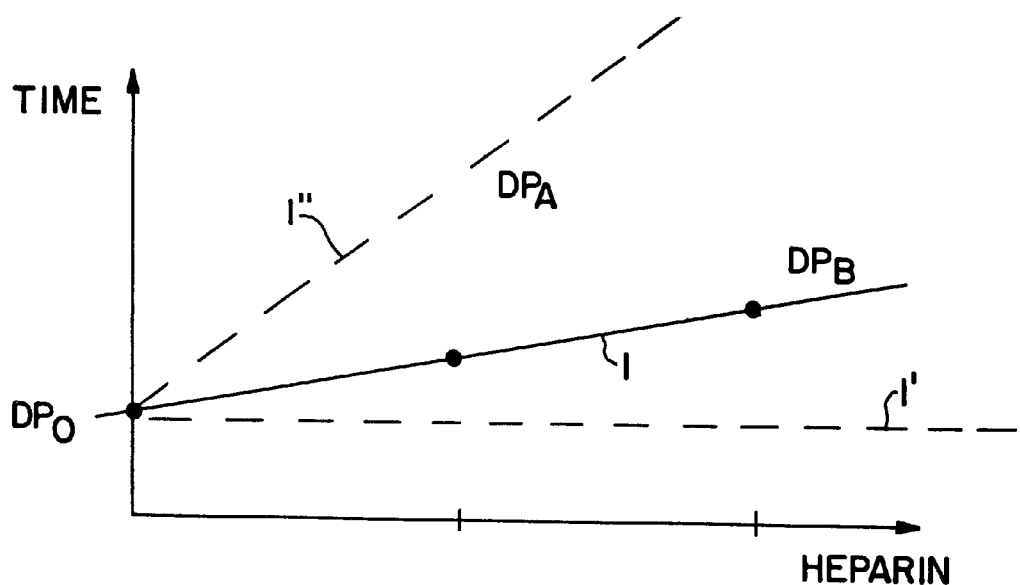
FIG. 1 is a graph for the clotting time of blood plotted against at least two levels of heparin, otherwise know as a heparin response curve according to the prior art.

FIG. 1 is a graph for the clotting time of blood plotted against at least two levels of heparin, otherwise know as a heparin dose response curve according to the prior art. As discussed above, such a graph may be created through the Medtronic HDR™ assay performed in the Medtronic HMS Plus™ Hemostasis Management System automated testing device. As known, such a test is used to test the response of a fresh, whole blood sample to a variety of heparin doses. As seen, at least three data points are collected, depicted here as DP-0, DP-A and DP-B.

The present invention takes advantage of the excess capability found in the current known Medtronic HMS Plus™ Hemostasis Management System, three data channels are used, while only two should actually be needed to ascertain the linear heparin dose response, and uses this excess channel capacity to concurrently create data of a heparin response with an additional amount of a blood factor which is involved with the coagulation cascade. Through such a system, data may be concurrently collected to both adjudge the heparin dose response, as well as the effect on such response to the addition of an added blood factor which is involved with the coagulation cascade. A graph which may be created with this invention is shown in FIG. 2.

Figure 2:
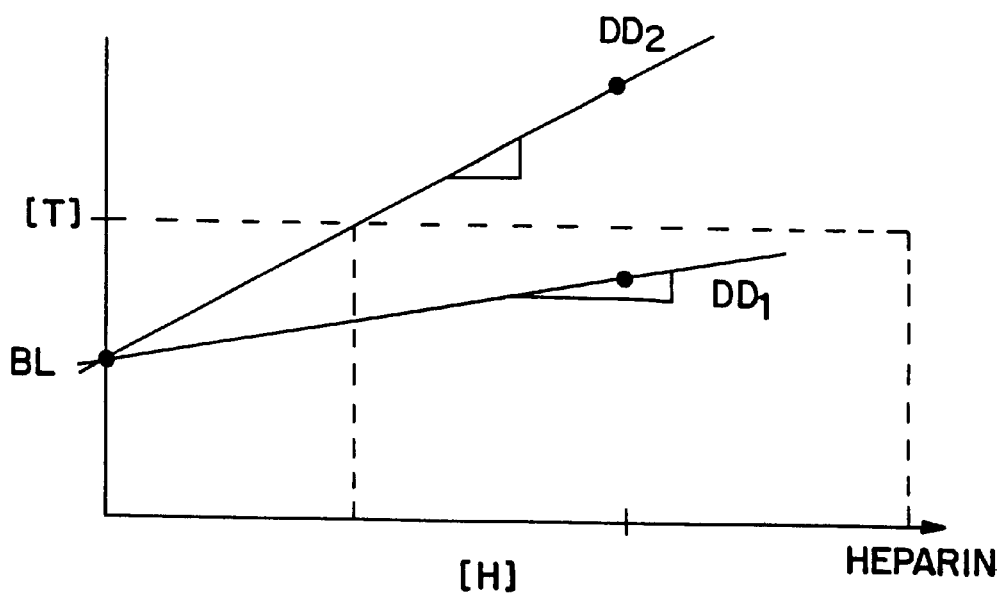
FIG. 2 is a graph for the clotting time of a sample of blood in which the heparin dose response is determined while the blood is provided with at least one level of a reagent that affect the anticoagulant activity of heparin.

FIG. 2 is a graph for the clotting time of a sample of blood in which the heparin dose response is determined while the blood is provided with at least one level of a reagent that affects the anticoagulant activity of heparin with a known amount of heparin. As seen, BL represents a baseline data point depicting the time required for a sample of fresh whole blood to clot in a specified channel or vial. Specific details of the channel or vial are described below. DD-1 represents a data point depicting the time required for a sample of fresh whole blood to clot in a specified channel or vial in the presence of a specified amount of heparin. DD-2 represents a data point depicting the time required for a sample of fresh whole blood to clot in a specified channel or vial in the presence of a specified amount of heparin and also in the presence of a blood factor that is involved with the coagulation cascade. In the preferred embodiment, this blood factor is AT III. While in this depiction the data point DD-2 is shown as above DD-1, the specific relationship between these data points will vary from patient to patient. In fact, it is this patient to patient variation which is the heretofore unmet need which the present invention meets.

Figure 3:
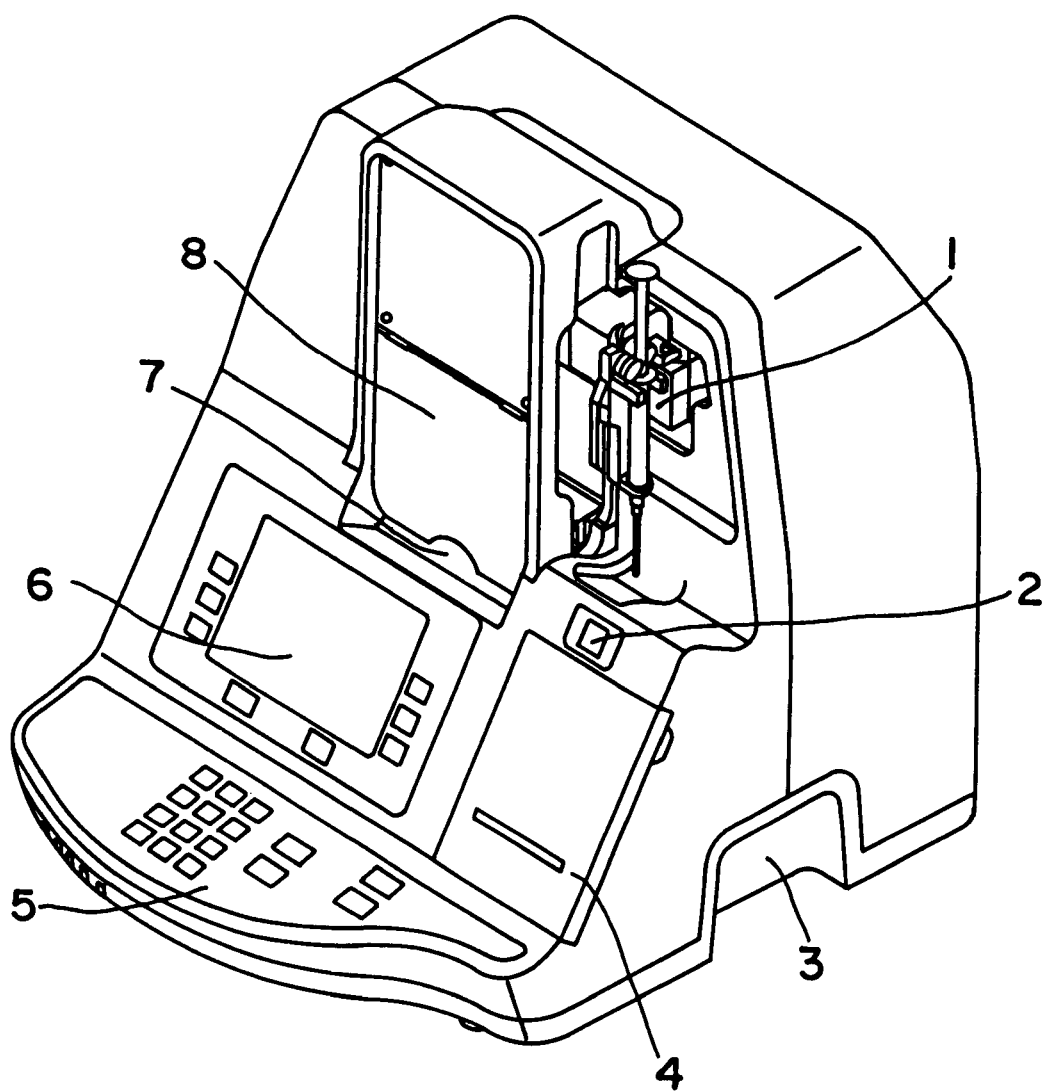
FIG. 3 is a perspective view of the Medtronic HMS Plus™ instrument within which a test or assay cartridge may be used.

FIG. 3 is a perspective view of the Medtronic HMS Plus™ instrument within which a test or assay cartridge may be used. The Hepcon HMS Plus is a microprocessor based, multi-channel clot timing instrument with automated syringe handling for pipetting blood into single use cartridges. It performs in vitro blood evaluations including heparin sensitivity evaluations, heparin assays, activated clotting times, and platelet function evaluations. As seen the Hepcon HMS Plus instrument includes a sample dispenser/syringe 1, a start/stop key 2, a carry handle 3, a printer 4, main keypad 5, LCD screen and keys 6, heat block and cartridge receiver 7, and a protective shield 8. The Hepcon HMS Plus instrument is available from Medtronic Inc., Minneapolis, Minn.

Figure 4:
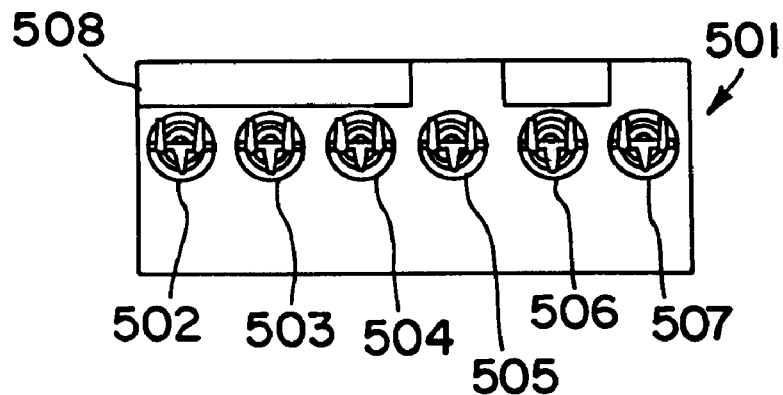
FIG. 4 is a top plan view of a test or assay cartridge 501 used with the instrument shown in FIG. 3 within which the present invention may be used.

FIG. 4 is a top plan view of a test or assay cartridge 501 used with the instrument shown in FIG. 3 within which the present invention may be used. As seen the cartridge 501 includes a plurality of channels 502–507. Positioned upon the top of housing is an optical code 508. The purpose of the optical codes is to let the HMS Plus™ instrument detect (via the software) what type of assay is being performed. Since there are a number of different assays which may be performed on the instrument, it is required which type of assay is to be performed so that the clotting data can be analyzed correctly. Of course a variety of other schemes could be used, as opposed to optical codes, such as user-input, magnetic, EEPROM, reflective or bar code.

Figure 5:
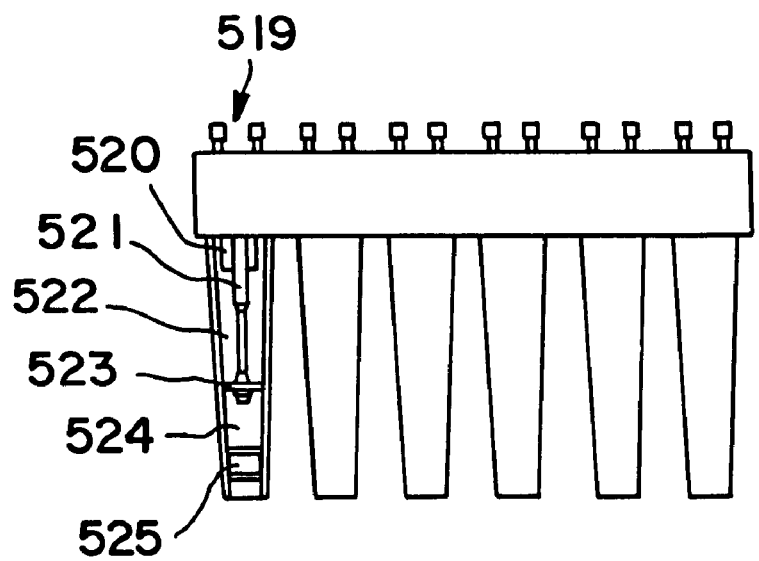
FIG. 5 is a side plan view of the cartridge 501 shown in FIG. 4.

FIG. 5 is a side plan view of the cartridge 501 shown in FIG. 4. As seen, each channel 502 contains a plunger 519. Plunger 519, extends above the upper surface of housing so as to be able to be actuated, upwardly and downwardly, by a testing device, such as the Medtronic HMS Plus™, discussed above. As further seen plunger 519, features plunger flag 520 along the upper portion. Plunger shaft 521 continues downwardly to daisy plug 523. Defined between daisy plug 523 and bottom plug 525 is reagent chamber 524. Thus, daisy plug 523 defines above it an upper reaction chamber 522, within which fresh whole blood is added, while daisy plug 523 defines below it the reagent chamber 524. As can be appreciated, movement of the plunger, and then the plunger daisy, upward removes the daisy plug from its position as shown and allows fluids within the reaction chamber 522 and reagent chamber 524 to mix.

As discussed above, the test of the current invention is carried out using a cartridge having a series of at least three separate channels. In the preferred embodiment, each channel is repeated at least once so that three channels, each repeated once, means six channels may be used. Each channel is constructed the same as that described above, although the compounds within the reaction and reagent chambers for each channel may vary (Further details may be found in U.S. Pat. No. 5,951,951, incorporated herein by reference).

In the preferred embodiment, the first channel chamber does not have, within the reaction chamber, any reagents. In the first channel reagent chamber, however, a solution is provided to promote contact activated coagulation. This is provided so as to accelerate coagulation because without such a compound the time required for a clot to form would be extensive In the second channel, the reagent chamber features, like the first channel, a solution to promote contact activated coagulation. The reaction chamber further has positioned within a primary reagent, such as a primary reagent to inhibit blood coagulation, preferably heparin. Preferably the heparin is provided in the amount of between approximately 0.1–10.0 Units/ml, and preferably in the amount to give a sample concentration of approximately 2.5 Units/ml. In the preferred embodiment, this heparin is provided in a dried form, dried to the inner surface of the reaction chamber such that it is dissolved upon contact with the fresh whole blood sample.

In the third channel, the reagent chamber features, like the first channel and the second channel, a solution to promote contact activated coagulation. The reaction chamber of the third channel further has positioned within a primary reagent, such as a primary reagent to inhibit blood coagulation, preferably heparin. Preferably the heparin is provided in the amount of between approximately 0.1–10.0 Units/ml, and preferably in the amount to give a sample concentration of approximately 2.5 Units/ml. In the preferred embodiment, this heparin is provided in a dried form, dried to the inner surface of the chamber such that it is dissolved upon contact with the fresh whole blood sample. The third channel further features, a blood factor which is involved with the coagulation cascade, and preferably a blood factor which targets proteases of the coagulation cascade, and in particular thrombin. In the preferred embodiment, this blood factor is AT III provided in the amount to give a sample concentration of between approximately 0.1–10.0 Units/ml, and preferably in the amount of approximately 0.8 Units/ml. In the preferred embodiment, this AT III is also provided in a dried form, dried to the inner surface of the reaction chamber such that it is dissolved upon contact with the fresh whole blood sample.

TABLE ONE

| Channel | Reagent chamber | Reaction chamber |
| --- | --- | --- |
| First channel | 12% kaolin in a buffered isotonic saline solution | — |
| Second channel | 12% kaolin in a buffered isotonic saline solution | 2.5 Units/ml Heparin |
| Third channel | 12% kaolin in a buffered isotonic saline solution | 2.5 Units/ml Heparin 0.8 U/ml AT III |

In use, it is important to note the order in which the channels are filled with sampled blood. Channels which contain anticoagulant are pipetted first and those which do not contain anticoagulant are filled last. This order or sequence prevents some premature activation of the baseline sample in the cartridge. That is, otherwise blood would be activated by the cartridge body while the other channels having coagulate were being filled. Even though the total time required for such fill is small, the effect on the blood and the test results is to be avoided.

Figure 6:
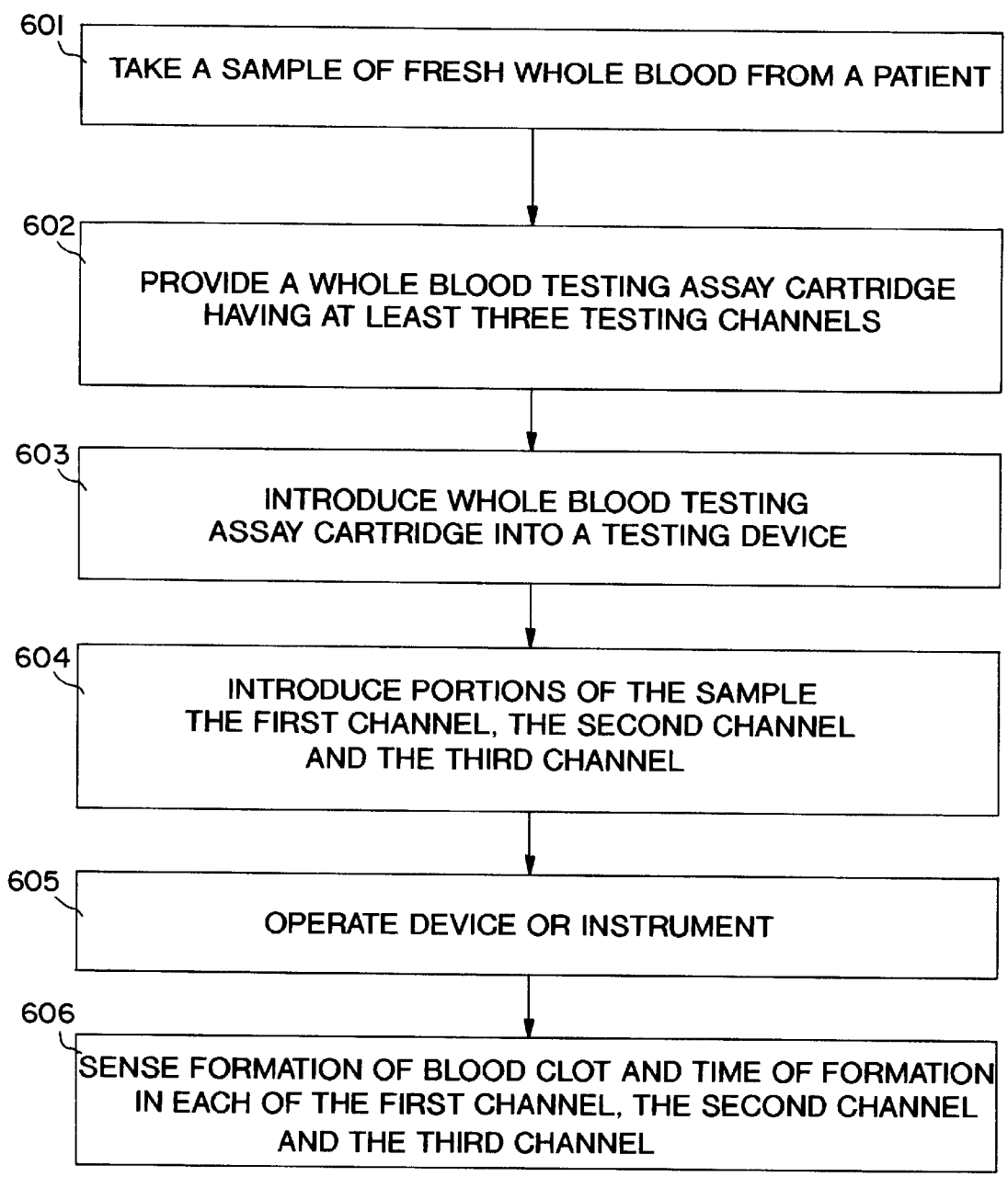
FIG. 6 depicts a method of determining whether a patient would benefit from the administration of a blood factor.

The present invention further encompasses a method of determining whether a patient would benefit from the administration of a blood factor. Such a method is depicted in FIG. 6. At 601 a sample of fresh whole blood is taken from a patient. At 602 a whole blood testing assay cartridge is provided, the cartridge having at least three testing channel. The cartridge is preferably constructed as described above with regards to FIG. 4. At 603, the cartridge is placed into the instrument. At 604, the instrument automatically introduces the sample into the assay cartridge. At 605 the instrument actuates the cartridge and begins testing for clot formation in the cartridge channels. The device operates to both mix the blood in each channel, preferably through the upward and downward movement of the plunger, as well as to sense the formation and presence of a blood clot. Next, at 606, the formation of a blood clot and its time of detection are sensed and noted for each of the first channel, second channel and the third channel. The times for each clot formation in each channel may thereafter be used to determine whether a patient would benefit from the administration of a blood factor prior to surgery. It should be noted, incidentally, that the instrument does not actually supply a plot of the resulting information, but rather merely computes the slope of the responses. The graph essentially illustrates what the instrument is doing via mathematical calculations. The comparison of the slopes, moreover, is made by the instrument and if the slope increases by more than 20%, the instrument gives an indication that the addition of AT III will be beneficial.

Although a specific embodiment of the invention has been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. A method for determining the response of a sample of a patient's whole blood to heparin in the presence and absence of antithrombin III the steps of:
   providing a first channel without heparin as a reagent therein and without antithrombin III as a reagent therein;
   providing a second channel with heparin as a primary reagent therein but without antithrombin III as a reagent therein;
   providing a third channel with heparin as a primary reagent and antithrombin III as a secondary reagent;
   adding a first portion from the sample of whole blood to the first channel;
   adding a second portion from the sample of whole blood to the second channel;
   adding a third portion from the sample of whole blood to the third channel; and
   determining the time required for a clot to be formed in each of the first, second and third channels.

2. The method according to claim 1 further comprising the step of mixing in the first channel the first portion from the sample of whole blood added to the first channel.

3. The method according to claims 1 further comprising the step of mixing together in the second channel the primary reagent and the second portion from the sample of whole blood added to the second channel.

4. The method according to claim 3 wherein the step of providing the second channel with a primary reagent comprises providing the primary reagent in a first concentration.

5. The method according to claim 1 further comprising the step of mixing together in the third channel the primary reagent, the secondary reagent and the third portion from the sample of whole blood added to the third channel.

6. The method according to claim 1 wherein the step of determining the time required for a clot to be formed in each of the first, second and third channels further comprises mixing in the first channel the first portion from the sample of whole blood added to the first channel, mixing together in the second channel the primary reagent and the second portion from the sample of whole blood added to second channel, mixing together in the third channel the primary reagent, the secondary reagent and the third portion from the sample of whole blood added to third channel and sensing the presence of a clot in each of the first, second and third channels.

7. The method according to claim 1 wherein the heparin is provided as the primary reagent in the amount of between approximately 0.1–10.0 Units/ml.

8. The method according to claim 7 wherein the heparin is provided as the primary reagent in the amount of approximately 2.5 Units/ml.

9. The method according to claim 1 wherein the antithrombin III is provided as the secondary reagent in the amount of between approximately 0.1–10.0 Units/ml.

10. The method according to claim 9 wherein the antithrombin III is provided as the secondary reagent in the amount of approximately 0.8 Units/ml.

11. A method for determining the response of a sample of a patient's whole blood to heparin in the presence and absence of antithrombin III comprising the steps of:

collecting blood coagulation time from a first set of data points sufficient to generate a first dose response line; at least one of the first set of data points provided by measuring a coagulation time of a portion of the sample of whole blood in the presence of heparin as a reagent and in the presence of antithrombin III as a reagent; the at least one of the first set of data points provided by:

providing a first channel with heparin as a primary reagent and antithrombin III as a secondary reagent;

adding a first portion from the sample of whole blood to the first channel;

mixing the sample of whole blood with the primary and secondary reagents in the first channel; and determining the time required for a clot to be formed in the first channel; and collecting blood coagulation time from a second set of data points sufficient to generate a second dose response line; at least one of the second set of data points provided by measuring a coagulation time of a portion of the sample of whole blood in the presence of heparin as a reagent and in the absence of antithrombin III as a reagent, the at least one of the second set of data points provided by:

providing a second channel with heparin as a primary reagent therein but without antithrombin III as a secondary reagent therein;

adding a second portion from the sample of whole blood to the second channel;

mixing the sample of whole blood with the primary reagent in the second channel; and determining the time required for a clot to be formed in the second channel.

12. The method according to claim 11 wherein the heparin is provided as the primary reagent in the amount of between approximately 0.1–10.0 Units/ml.

13. The method according to claim 12 wherein the heparin is provided as the primary reagent in the amount of approximately 2.5 Units/ml.

14. The method according to claim 11 wherein the antithrombin III is provided as the secondary reagent in the amount of between approximately 01–10.0 Units/ml.

15. The method according to claim 14 wherein the antithrombin III is provided as the secondary reagent in the amount of approximately 0.8 Units/ml.

* * * * *

UNITED STATES PATENT AND TRADEMARK OFFICE
CERTIFICATE OF CORRECTION

PATENT NO. : 6,541,262 B1
APPLICATION NO. : 09/560470
DATED : April 1, 2003
INVENTOR(S) : Baugh et al.

It is certified that error appears in the above-identified patent and that said Letters Patent is hereby corrected as shown below:

Column 6, line 40, that portion of the claim reading "antithrombin III the" should read --antithrombin III comprising the--.

Column 8, line 33, that portion of the claim reading "01-10.0 Units/ml." should read --0.1-10.0 Units/ml.--.

Signed and Sealed this

First Day of May, 2007

JON W. DUDAS
*Director of the United States Patent and Trademark Office*